(12) United States Patent
Lokhandwalla et al.

(10) Patent No.: US 7,299,806 B2
(45) Date of Patent: Nov. 27, 2007

(54) COMPLIANT PROBE INTERFACE ASSEMBLY

(75) Inventors: Murtuza Lokhandwalla, Watervliet, NY (US); Ajay Kapur, Clitton Park, NY (US)

(73) Assignee: General Electric Company, Niskayuna, NY (US)

( * ) Notice: Subject to any disclaimer, the term of this patent is extended or adjusted under 35 U.S.C. 154(b) by 722 days.

(21) Appl. No.: 10/723,571

(22) Filed: Nov. 25, 2003

(65) Prior Publication Data

US 2005/0113684 A1    May 26, 2005

(51) Int. Cl.
*A61B 8/00* (2006.01)
(52) U.S. Cl. .................. 128/915; 600/445; 600/446
(58) Field of Classification Search ............... 600/427, 600/445, 446; 378/37; 128/915
See application file for complete search history.

(56) References Cited

U.S. PATENT DOCUMENTS

| | | | |
|---|---|---|---|
| 3,971,950 A | 7/1976 | Evans et al. | |
| 4,271,706 A | 6/1981 | Ledley | 73/614 |
| 4,715,228 A | 12/1987 | Livsey et al. | |
| 5,094,243 A | 3/1992 | Puy et al. | 128/662.03 |
| 5,474,072 A | 12/1995 | Shmulewitz | |
| 5,479,927 A | 1/1996 | Shmulewitz | |
| 5,640,956 A | 6/1997 | Getzinger et al. | |
| 5,664,573 A | 9/1997 | Shmulewitz | |
| 5,851,180 A | 12/1998 | Crosby et al. | |
| 5,855,554 A | 1/1999 | Schneider et al. | |
| 5,938,613 A * | 8/1999 | Shmulewitz | 600/461 |
| 5,983,123 A | 11/1999 | Shmulewitz | |
| 6,425,865 B1 * | 7/2002 | Salcudean et al. | 600/437 |
| 6,574,499 B1 * | 6/2003 | Dines et al. | 600/427 |
| 2002/0173722 A1 | 11/2002 | Hoctor et al. | |
| 2003/0167004 A1 | 9/2003 | Dines et al. | |

OTHER PUBLICATIONS

Patent Abstracts of Japan, vol. 011, No. 287 (p. 617), Sep. 17, 1987 & JP 62 083651 (Mitshuishi Electric Corp), Apr. 17, 1987.
E. Kelly-Fry and V.P. Jackson, *Adaptation development and expansion of x-ray mammography techniques for ultrasound mammography*, Ultrasound Med., 1991, 10: p. S-16.

* cited by examiner

*Primary Examiner*—Eleni Mantis Mercader
*Assistant Examiner*—Jacqueline Cheng
(74) *Attorney, Agent, or Firm*—Jenifer E. Haeckl; Jean K. Testa

(57) ABSTRACT

A probe interface assembly for an automated medical imaging system is provided. The assembly comprises a platform including and inner frame for supporting an ultrasound probe in spaced apart relationship relative to a compression paddle arranged to apply a compression load to breast tissue being scanned during a medical imaging process. The platform is adapted to contactively engage the compression paddle during the medical imaging process. The platform may include a first resilient pivot connection at each side of a first set of mutually opposite sides of said inner frame to provide a tilt degree of freedom about a first axis. The platform may further include a second resilient pivot connection at each side of a second set of mutually opposite sides of the inner frame to provide a tilt degree of freedom about a second axis positioned orthogonal relative to the first axis. The first and second connections allow a face of the probe to remain substantially parallel relative to the compression paddle notwithstanding of deformation of the compression paddle that may occur when the compression paddle applies the compression load to the tissue being scanned.

15 Claims, 3 Drawing Sheets

COMPLIANT PROBE INTERFACE ASSEMBLY

This invention was made with U.S. Government support through Government Contract Number-RO1-CA-91713-01A1 awarded by the National Institute of Health, and, in accordance with the terms set forth in said contract, the U.S. Government may have certain rights in the invention.

BACKGROUND OF THE INVENTION

The present invention is generally related to a probe interface assembly, and, more particularly, to a compliant probe interface assembly for imaging breast tissue with an ultrasound probe in conjunction with X-ray mammography, and thereby provide geometrically registered X-ray and ultrasound images.

FIG. 1 illustrates a schematic of conventional X-ray mammographic equipment combined with an ultrasound scanning system. This usually includes a compression plate 10 (e.g., a plate made up of polycarbonate such as Lexan or other suitable materials) to compress and flatten breast tissue 12 against a detector plate 18. In order to perform an ultrasound scan subsequent to an X-ray mammogram, the system further includes an ultrasound probe 14, as may be positioned to traverse atop such a plate to generate ultrasonic images of the internal structure of the breast tissue. A gel 16 may be provided as shown in FIG. 1. The gel typically comprises a suitable composition for reducing acoustic impedance mismatch and reflectance at the plate/probe interface. Ideally, the compression action should provide uniform contact of the breast tissue with the compression plate to achieve appropriate ultrasound propagation as well as superior X-ray imaging.

In practice, the compressing surface of the compression plate may deform when exposed to typical mammographic breast compression forces. The resulting maximum deflection of the plate, as may be measured from a horizontal plane, should be typically constrained to lie within 1 cm, as per MQSA requirements. Since the ultrasound probe 14 rides on top of this deformed plate, as shown in FIG. 1, the ultrasonic beam propagates through a non-uniform gap and a non-parallel surface.

A varying gap changes the ultrasound path between the probe and the compression plate and leads to inconsistent attenuation. A non-parallel surface may lead to variable beam refraction, as the ultrasound beam may be formed from multiple elements in a linear array ultrasound probe. Each of these conditions could have adverse effects on the ultrasound image quality. These conditions may also make it burdensome for a radiologist to correlate an X-ray image to an ultrasound image due to the lack of a consistently reproducible setup from one scan to the next scan.

To avoid such adverse effects, it would be desirable to maintain a uniform gap and/or parallel alignment between the probe face and the compression plate. For example, this would allow keeping a desired profile of ultrasound beam incident angles on the compressive plate so that corrective time delays, as may be generated by a beam-forming processor during transmit and receive modes, will correctly adjust the beam summation to correct for refractive effects through the compression plate.

Early attempts to use ultrasound for breast imaging involved conventional handheld scanning of the free uncompressed breast. Since such a handheld ultrasound imaging does not provide geometric registration with the X-ray images, it is difficult to compare the features obtained in each image since these may belong to different regions of the breast. Hence, there is a need for a system that performs X-ray and an automated ultrasound scan in a single patient setting.

Known automated scanning systems have failed to effectively solve the issues arising from a varying gap and a non-parallel surface. One known attempt was to position the ultrasound probe at the farthermost location (height) from the deformed plate. Although this positioning would ensure that the deformed plate would not obstruct the probe during the course of the scan, the resulting variation in probe-plate distance along the face of the transducer would deteriorate image quality. One conceptual possibility would have been creating a compression plate constructed of special materials and/or geometry to be sufficiently rigid to avoid deformation in the presence of compression loads, and at the same time be sufficiently radio- and sono-lucent to allow passage to the x-rays and ultrasound beams. In practice, however, cost-effective materials and plate configurations suitable for a combined mammographic and ultrasonic examination will inevitably bow to some degree.

Another drawback of known automated scan systems is that they do not have the flexibility of a handheld system to orient the probe at any desired orientation with respect to a region of interest and at the same time maintaining contact with the bowed compression plate. An ultrasound transducer could have a higher resolution along its lateral axis as compared to its elevation axis. Hence, it would be desirable that the probe lateral axis be aligned nominally with the direction of orientation of the specific structure that needs to be resolved.

BRIEF DESCRIPTION OF THE INVENTION

Generally, the present invention fulfills the foregoing needs by providing, in one aspect thereof, an apparatus for positioning an ultrasound probe relative to a compression plate such that the probe face is generally parallel and at a fixed distance from the compression plate.

In another aspect thereof, the present invention further fulfills the foregoing needs by providing a means to track the orientation and displacement of the probe surface from a nominal plane surface by providing appropriate sensors.

In yet another aspect, a means for orienting the probe about its longitudinal axis is provided and hence aligning the higher resolution direction of the probe with an expected orientation of breast structures to be scanned.

BRIEF DESCRIPTION OF THE DRAWINGS

The features and advantages of the present invention will become apparent from the following detailed description of the invention when read with the accompanying drawings in which.

DETAILED DESCRIPTION OF THE INVENTION

The inventors of the present invention have innovatively recognized a probe interface assembly for compliantly supporting an ultrasound probe to accurately and consistently conform with respect to a compression paddle in an automated breast ultrasound scan system. In some imaging diagnostics applications, the ultrasound scan may be performed in conjunction with X-ray mammographic equipment that may be integrated with the breast ultrasound scan system. Aspects of the present invention enable accurate, reproducible ultrasound images reducing distortion and attenuation, which may be introduced as a consequence of combining the ultrasound scanning with X-ray mammography.

As described in greater detail below, the probe interface assembly provides sufficient degrees of freedom to mimic the versatility of a free-hand scan while providing a consistently reproducible and automated setup suitable for generating high quality imaging. In one exemplary embodiment, the probe interface assembly may provide two rotational and one translation degree of freedom.

Figure 1:
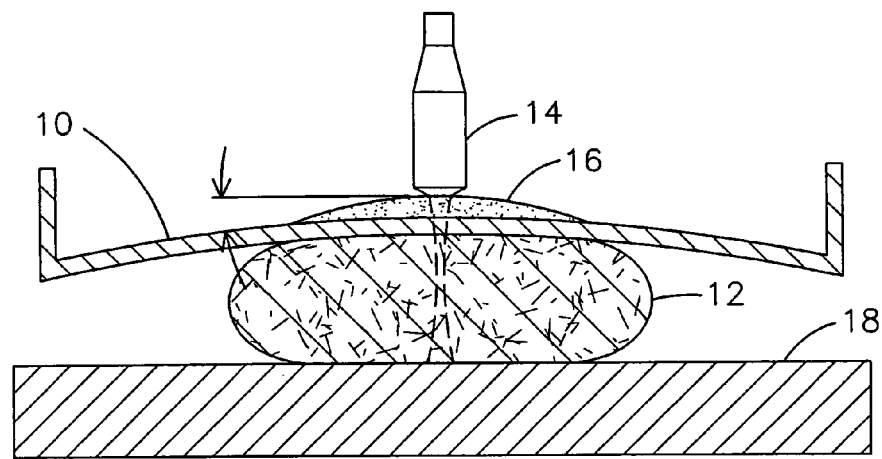
FIG. 1 in part illustrates a cross-sectional view of components of an exemplary automated breast imaging system including a compression plate that may deflect when subjected to compression forces during a scan of breast tissue.
Figure 2:
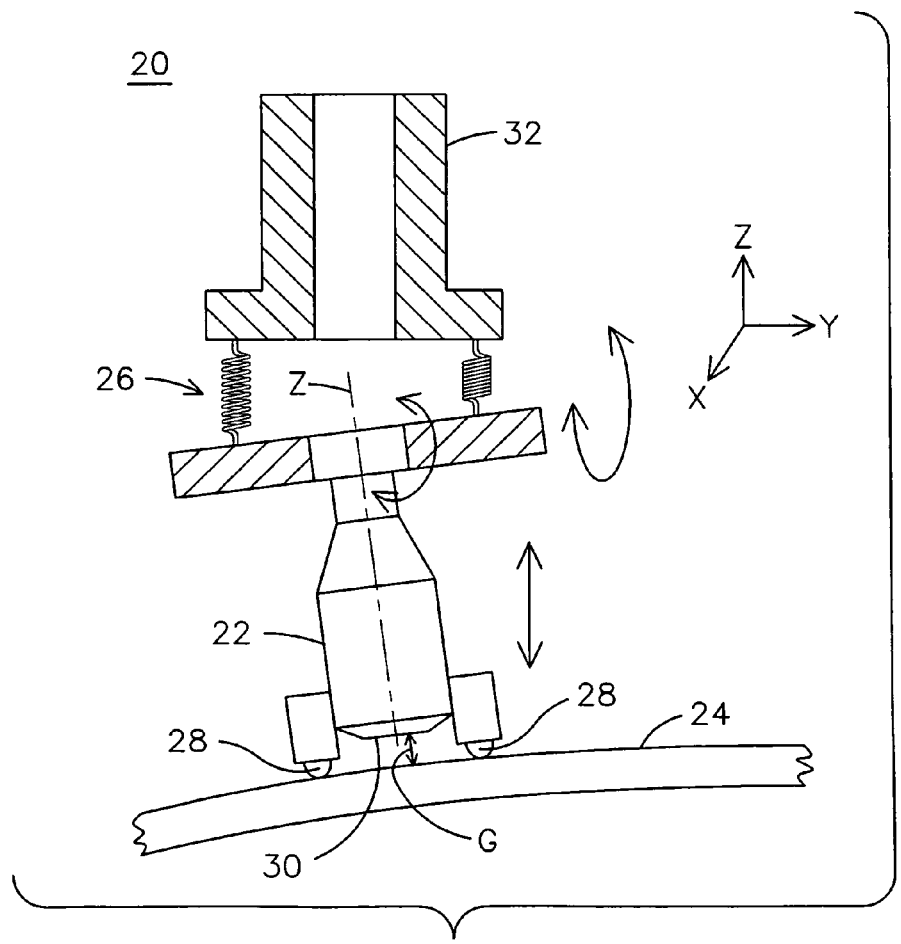
FIG. 2 is a conceptual schematic representation of a probe interface assembly embodying aspects of the present invention for flexibly holding an ultrasound probe to conform with respect to a compression paddle, such as that of FIG. 1.

In one exemplary embodiment, as illustrated in the conceptual schematic representation of FIG. 2, a probe interface assembly 20 for compliantly holding an ultrasound probe 22 to conform with respect to a compression paddle 24 comprises: an articulated mounting platform 26 and a set of paddle-contacting elements, e.g., rollers/spheres 28 proximate to a probe face 30 and positioned to engage a corresponding surface of the compression paddle 24. In one aspect of the present invention, the articulated mounting platform 26 and the rollers/spheres 28 allow the probe face to conformably tilt and/or move along a longitudinal axis Z to remain parallel and at a fixed distance from the compression paddle. For example, this allows maintaining a constant and reduced gap G between the probe face 30 and paddle 24, hence reducing variation in attenuation and refraction effects that could otherwise affect overall image quality.

Figure 3:
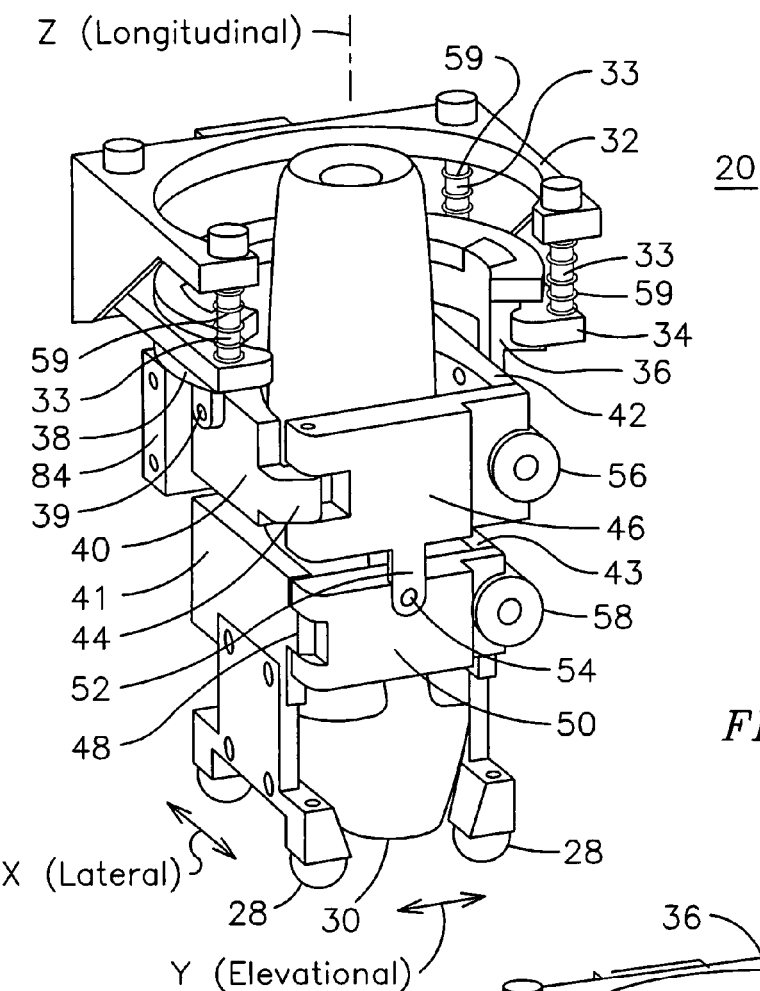
FIG. 3 is an isometric view of one exemplary embodiment of a probe interface assembly embodying aspects of the present invention.

FIG. 3 is an isometric view of an exemplary embodiment of probe interface assembly 20. A holder 32 may be mechanically connected in conventional fashion to motorized drives (not shown) that allow translating probe interface assembly 20 over the paddle 24 relative to a lateral axis X and an elevation axis Y mutually orthogonal relative to one another and to the longitudinal axis Z. In one exemplary embodiment, holder 32 supports (e.g., through a plurality of connecting rods 33) a non-rotatable frame 34 that provides slidable support relative to a rotatable frame 36. That is, rotation of the probe 22 about the longitudinal axis Z may be provided through angular rotation of rotatable frame 36 relative to non-rotatable frame 34.

Non-rotatable frame 34 further supports a bracket 38 configured to provide a spring biased pivotal connection 39 (e.g., a torsion spring or any other suitable biasing device and/or material) to a first lateral frame 40 spaced apart from the non-rotatable frame 34 and from a second lateral frame 41 beneath first lateral frame 40. That is, lateral frame 40 is pivotable through pivotal connection 39 relative to the elevation axis Y. It will be appreciated that another set of lateral frames 42 and 43 spaced apart from and opposite to lateral frames 40 and 41 may be arranged to provide the same operational and/or structural relationships described above in connection with lateral frames 40 and 41.

Figure 4:
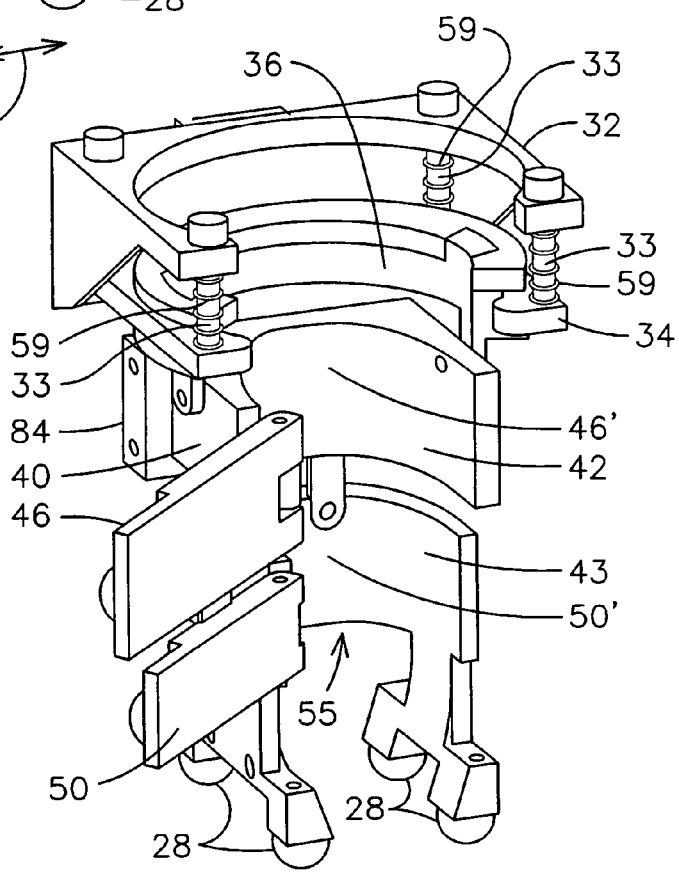
FIG. 4 shows additional exemplary details regarding the probe interface assembly of FIG. 3.

In one exemplary embodiment, first lateral frame 40 provides a first hinged support 44 to a first frontal frame 46, and second lateral frame 41 further provides a second hinged support 48 to a second frontal frame 50 spaced apart beneath first frontal frame 46. In one exemplary embodiment, first frontal frame 46 includes a pivot arm 52 providing a spring biased pivotal connection 54 (e.g., a torsion spring or any other suitable biasing device and/or material) to second frontal frame 50. That is, frontal frames 46 and 50 are pivotable through pivotal connection 54 relative to the lateral axis X. It will be appreciated that a set of rear frames 46' and 50' spaced apart from and opposite to frontal frame 46 and 50 may be arranged to provide the same pivoting capability described above in connection with frontal frames 46 and 50. In one exemplary embodiment, as shown in FIG. 4, top rear frame 46' may be integrally constructed with lateral frames 40 and 42, and bottom rear frame 50' may be integrally constructed with lateral frames 41 and 43.

In one exemplary embodiment, the spaced apart lateral frames together with the spaced apart frontal and rear frames define a platform 55 for tightly receiving and supporting the ultrasound probe 22. That is, the ultrasound probe when positioned inside the platform will follow any tilting and/or translation movements experienced by the platform. For example, the interior surfaces of the lateral frames, the frontal frames and the rear frames may be contoured to match the corresponding contour of the probe. Respective knobs 56 and 58 may allow an operator to swivel frontal frames 46 and 50 to an open position as shown in FIG. 4, e.g., to place the ultrasound probe into the platform or to remove the probe from the platform. Once the probe is positioned in such a platform, the operator would swivel frontal frames 46 and 50 to a closed position, as shown in FIG. 3. It is contemplated that in some applications the ultrasound probe could be integrally constructed within the platform 55, e.g., integrally molded or integrated therein using any other suitable manufacturing technique.

Figure 5:
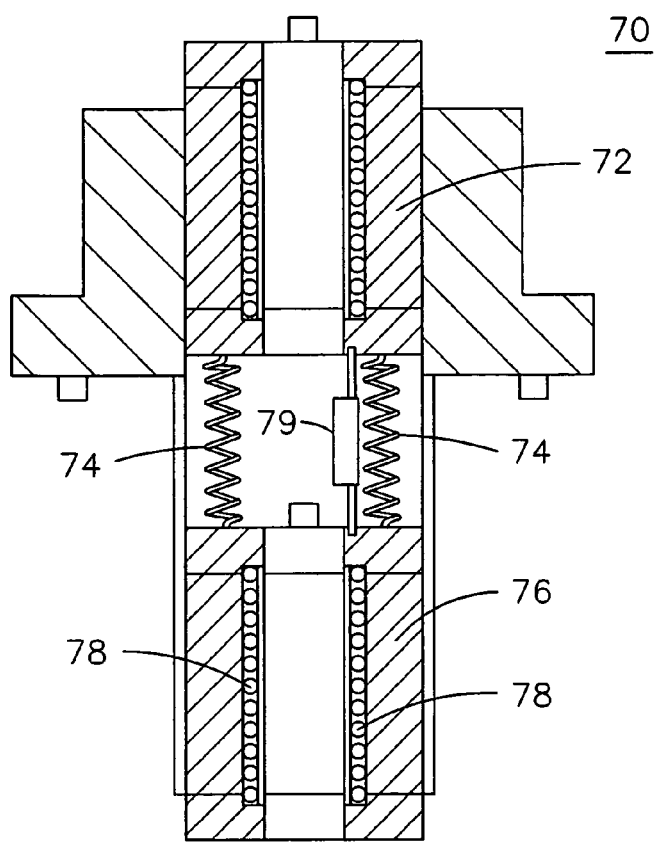
FIG. 5 is a cross-sectional view of one exemplary suspension mechanism for a probe interface assembly embodying aspects of the present invention.
Figure 6:
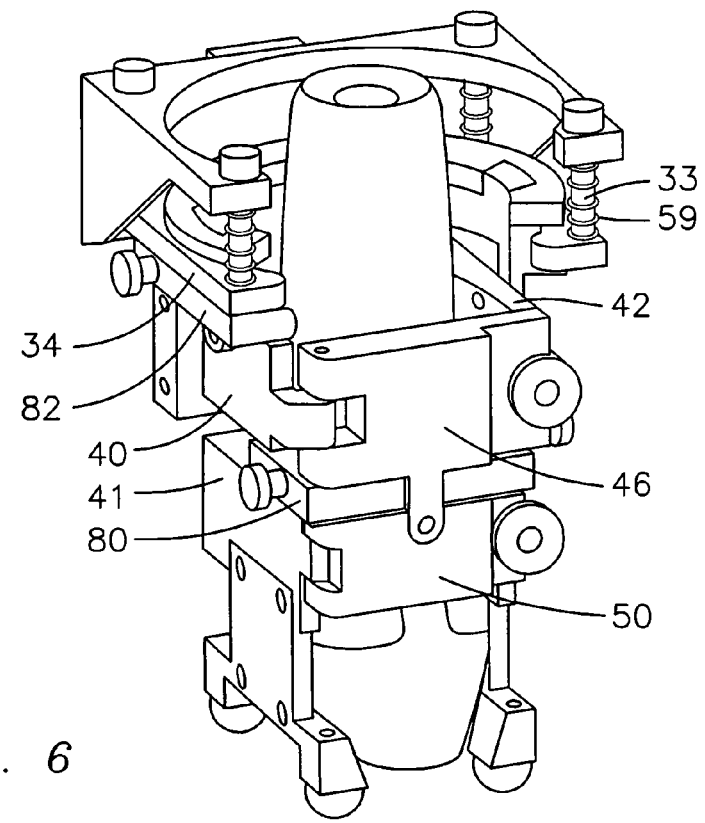
FIG. 6 illustrates means for optionally blocking tilting motion in a probe interface assembly embodying aspects of the present invention.

In one exemplary embodiment, connecting rods 33 may include springs 59 or may comprise hollow rods including respective bushings or any other suitable biasing device and/or material to provide a degree of freedom along the longitudinal axis Z. For example, height surface changes in the compression paddle would cause an upward force through the rollers to the platform that supports the probe. This upward force would cause the platform and probe to move upwardly along the longitudinal axis to maintain the constant gap G between the probe and the compression paddle regardless of height variation of the paddle. In essence, connecting rods 33 and springs 59 in this embodiment would act analogous to a suspension system configured to accept displacements along the longitudinal axis. As will be appreciated by those skilled in the art, other implementations will work equally effective to provide a suspension system along the longitudinal axis. For example, as shown in FIG. 5, the rear of the platform may be designed to support a suspension mechanism 70 connectable to a vertical shaft (not shown) and comprising, for example, a first stationary section 72 coupled through springs 74 to a second slidable section 76 that allows displacements along the longitudinal axis by way of bearings 78.

In one exemplary embodiment, the probe interface assembly 20 has a means for optionally blocking the above-described tilting capability. For example, as shown in FIG.

6, a first clamp 80 may be wedged or otherwise positioned within the spacing between frontal frames 46 and 50 to prevent tilting movement relative to the lateral axis X. Similarly, a second clamp 82 may be inserted within the spacing between non-rotatable frame 34 and lateral frame 40 to prevent tilting movement relative to the elevation axis Y. Similarly, once the operator has rotated the probe/platform to a desired angular position about the longitudinal axis Z, a locking mechanism would be used to maintain the desired angular position during a scan.

In one exemplary embodiment, a bi-axial tilt sensor, e.g., made up of a pair of LVDT's (linear voltage differential transformers) positioned orthogonal to one another, may be used to measure the inclination of the probe relative to the lateral and elevation axes. One of such a pair of LVDT devices is identified by numeral reference 84 in FIG. 3. A third LVDT 79 (as illustrated in FIG. 5) can be used to determine the relative linear displacement of the probe along the longitudinal Z axis. Such a translation sensor may, for example, be positioned to sense the relative translation motion (e.g., along the Z axis) between fixed holder 32 and translatable frame 34 (FIG. 3), or between stationary section 72 and sliding section 76 (FIG. 5). It is realized that this translational data can be, in an alternative embodiment, derived from the tilt measurements coupled with the position information, rendering the need of this third LVDT superfluous. However, this data would still deemed to be useful for applications where the tilting motions could be blocked and only sliding motion is permitted. The tilt and sliding measurements may be collected and stored in a suitable memory as the probe scans the breast tissue so that such inclination can be accounted for during image reconstruction, as may be performed by a suitable processor. Aspects of the present invention will enable ultrasound imaging in combination with X-ray mammography with highly versatile, and reproducible probe positioning to view breast structures with greater clarity and image quality as compared to that achieved with conventional handheld scanning.

In operation, probe interface assembly 20 provides a means to automatically and accurately orient/position the probe with respect to the deformed compression paddle. Exemplary features of the probe interface assembly may include:

A means to enable the probe to rotate, translate or both—referred to as a compliant probe interface or articulated mounting platform. The assembly may have two pairs of pivots located in two axes (e.g., lateral and elevation axes) perpendicular to each other and to the longitudinal axis of the probe. The pivots may comprise a torsional spring built-in at the pivotal connections to enable the assembly to self-center. The assembly may also include a degree of freedom along the longitudinal axis to accommodate height variation of the paddle.

A set of rollers/spheres located near the probe surface allow contacting the compression paddle. The rollers/spheres essentially track the deformed paddle surface and pass the reaction forces to the articulated platform maintaining the probe surface parallel and at a fixed distance with respect to the deformed paddle surface.

A biaxial tilt sensor and a displacement sensor may be used to measure the angular orientation and the relative displacement of the probe relative to a planar reference as the probe traverses the compression paddle.

Ability to rotate the probe about its longitudinal axis. In one exemplary embodiment, the probe may preferably be oriented with its elevation axis perpendicular to the chest wall since the probe may have a higher image resolution along the elevation axis. Thus, in order to scan structures that may be arbitrarily oriented in the breast tissue, it would be desirable to be able to selectively rotate the probe about its longitudinal axis. This may allow improved visibility of areas that may not necessarily be under the probe axis having the highest imaging resolution. Examples of such areas may be the walls of breast ducts in which carcinomas tend to develop and from where they may spread to surrounding tissues. The ducts tend to converge from the lobular end units to the nipple region and thus if the probe were to scan the breast in a direction parallel to the elevation axis, which may be substantially perpendicular to the ducts, the resulting beam resolution may not be the highest, and possibly rendering insufficient image clarity. However, a probe that is rotatable about its longitudinal axis to a desired angular position prior to scanning would advantageously bring the ductal walls into a region beneath the probe that may then utilize the probe's superior lateral or axial resolution capabilities. Alternatively, the probe may be positioned at any given position on the compression paddle and then rotated about the longitudinal axis in the same position to achieve the same result for just that region of interest. The above exemplary features of the present invention provide versatility comparable to that of a prior art handheld ultrasound scan while making such a scan more reproducible and accurate.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. An automated imaging system for scanning breast tissue during a medical imaging process, said system comprising:
    a compression paddle arranged to apply a compression load to breast tissue being scanned during said medical imaging process; and
    a probe interface assembly comprising:
        a platform including an inner frame for supporting an ultrasound probe in spaced apart relationship relative to the compression paddle, said platform adapted to contactively engage said compression paddle during said medical imaging process, said platform including a first resilient pivot connection at each side of a first set of mutually opposite sides of said inner frame to provide a tilt degree of freedom about a first axis, said platform further including a second resilient pivot connection at each side of a second set of mutually opposite sides of said inner frame to provide a tilt degree of freedom about a second axis positioned orthogonal relative to said first axis, said first and second connections allowing a face of said probe to remain parallel relative to the compression paddle notwithstanding of deformation of the compression paddle that may occur when said compression paddle applies the compression load to the tissue being scanned.

2. The imaging system of claim 1 wherein said platform is coupled to a rotatable frame configured to provide a rotational degree of freedom to the platform about a third axis perpendicular to said first and second axes.

3. The imaging system of claim 2 wherein said platform is coupled to a suspension device configured to provide a translation degree freedom to said platform along said third axis.

4. The imaging system of claim 1 further comprising a tilt sensor arranged to measure a respective degree of tilt of the platform relative to said first and second axes.

5. The imaging system of claim 1 wherein said platform includes a first aperture for receiving a clamp adapted to block the tilt degree of freedom about said first axis.

6. The imaging system of claim 1 wherein said platform further includes a second aperture for receiving a clamp adapted to block the tilt degree of freedom about said second axis.

7. The imaging system of claim 1 comprising in combination an X-ray mammography system and an ultrasound imaging system.

8. A probe interface assembly for an automated medical imaging system, said assembly comprising:

a platform including and inner frame for supporting an ultrasound probe in spaced apart relationship relative to a compression paddle arranged to apply a compression load to breast tissue being scanned during a medical imaging process, said platform adapted to contactively engage said compression paddle during said medical imaging process, said platform including a first resilient pivot connection at each side of a first set of mutually opposite sides of said inner frame to provide a tilt degree of freedom about a first axis, said platform further including a second resilient pivot connection at each side of a second set of mutually opposite sides of said inner frame to provide a tilt degree of freedom about a second axis positioned orthogonal relative to said first axis, said first and second connections allowing a face of said probe to remain parallel relative to the compression paddle notwithstanding of deformation of the compression paddle that may occur when said compression paddle applies the compression load to the tissue being scanned.

9. The probe interface assembly of claim 8 wherein said platform is coupled to a rotatable frame configured to provide a rotational degree of freedom to the platform about a third axis perpendicular to said first and second axes.

10. The probe interface assembly of claim 9 wherein said platform is coupled to a suspension device configured to provide a translation degree freedom to said platform along said third axis.

11. The probe interface assembly of claim 8 further comprising a tilt sensor arranged to measure a respective degree of tilt of the platform relative to said first and second axes.

12. The probe interface assembly of claim 8 wherein said platform includes a first aperture for receiving a clamp adapted to lock the tilt degree of freedom about said first axis.

13. The probe interface assembly of claim 8 wherein said platform further includes a second aperture for receiving a clamp adapted to lock the tilt degree of freedom about said second axis.

14. A probe interface assembly for an automated medical imaging system, said assembly comprising:

a platform including and inner frame for supporting an ultrasound probe in spaced apart relationship relative to a compression paddle arranged to apply a compression load to breast tissue being scanned during a medical imaging process, said platform adapted to contactively engage said compression paddle during said medical imaging process, said platform coupled to a rotatable frame configured to provide a rotational degree of freedom to the platform about a longitudinal axis of said probe, wherein said rotational degree of freedom enables alignment between a higher resolution axis of the probe and an expected orientation of structures in the breast tissue to be scanned.

15. A probe interface assembly for an automated medical imaging system, said assembly comprising:

a platform including an inner frame for supporting an ultrasound probe in spaced apart relationship relative to a compression paddle arranged to apply a compression load to breast tissue being scanned during a medical imaging process, said platform adapted to contactively engage said compression paddle during said medical imaging process, said platform coupled to a suspension device configured to provide a translation degree freedom to said platform along a longitudinal axis to accommodate height variation of the compression paddle.

* * * * *